(12) United States Patent
Langley et al.

(10) Patent No.: US 8,633,713 B2
(45) Date of Patent: Jan. 21, 2014

(54) INTERNAL PIPE COATING INSPECTION ROBOT

(75) Inventors: Russell Langley, Adair, OK (US);
James A. Huggins, Watts, OK (US);
John D. Carter, Catoosa, OK (US);
David Paulley, Milton Keynes (GB);
Keith R. Roberts, Manford, OK (US);
Darrell L. Davis, Broken Arrow, OK (US); Michael E. O'Neill, Tulsa, OK (US); Steve D. Hayes, Tulsa, OK (US);
Dale G. Davis, Beggs, OK (US); John D. Lindemann, Broken Arrow, OK (US)

(73) Assignee: CRTS, Inc., Tulsa, OK (US)

( * ) Notice: Subject to any disclaimer, the term of this patent is extended or adjusted under 35 U.S.C. 154(b) by 466 days.

(21) Appl. No.: 13/084,035

(22) Filed: Apr. 11, 2011

(65) Prior Publication Data

US 2012/0256643 A1 Oct. 11, 2012

(51) Int. Cl.
*G01R 27/26* (2006.01)
(52) U.S. Cl.
USPC ........... 324/663; 324/600; 324/667; 73/865.8
(58) Field of Classification Search
None
See application file for complete search history.

(56) References Cited

U.S. PATENT DOCUMENTS

| | | | |
|---|---|---|---|
| 3,170,113 A | 2/1965 | Harmon | |
| 3,243,697 A | 3/1966 | Schmidt | |
| 3,251,134 A | 5/1966 | Wojcik | |
| 4,295,092 A | 10/1981 | Okamura | |
| 4,986,314 A | 1/1991 | Himmler | |
| 5,181,962 A | 1/1993 | Hart | |
| 5,746,905 A | 5/1998 | Murray | |
| 6,931,149 B2 | 8/2005 | Hagene et al. | |
| 7,077,020 B2 * | 7/2006 | Langley et al. | 73/865.8 |
| 7,131,344 B2 | 11/2006 | Tarumi | |
| 7,493,817 B2 | 2/2009 | Germata | |
| 2004/0207394 A1 * | 10/2004 | Harthorn et al. | 324/216 |
| 2007/0006670 A1 | 1/2007 | Brown et al. | |

* cited by examiner

*Primary Examiner* — Jermele M Hollington
*Assistant Examiner* — Trung Nguyen
(74) *Attorney, Agent, or Firm* — Senniger Powers LLP

(57) ABSTRACT

There is provided herein a robot-based electrical system for locating holidays within coated pipe that does not utilize a grounding wire. In a preferred arrangement, the robot will carry a metal rotating brush/capacitive pad combination and changes in the capacitance in the brush/pad circuit will be used to identify imperfections in the interior coating of the pipe and especially those located proximate a girth weld. In another preferred embodiment, a circumferential brush will be used that allows testing of the integrity of the internal coating throughout the length of the pipe as the robot travels the pipeline.

20 Claims, 4 Drawing Sheets

INTERNAL PIPE COATING INSPECTION ROBOT

FIELD OF THE INVENTION

The present invention relates generally to the field of the inspection of pipe and, more particularly, to the field of robotic inspection of internal coatings in large diameter pipe such as that used in pipelines to transport crude oil and other fluids.

BACKGROUND OF THE INVENTION

Large diameter pipe such as that used to transmit substances such as oil and gas is manufactured in sections that are a few tens of feet in length. Pipe diameters can vary considerably but typically are between about 5 and 72 inches in diameter, although diameters outside of that range are known. Pipelines are constructed from individual metallic pipes (sections) which are laid individually end to end and then joined to one another by means of a welded connection. Pipelines can extend for many miles in length and are expected to last for years. Additional information related to the general environment of the instant invention can be found in, for example, U.S. Pat. No. 7,077,020, the disclosure of which is incorporated herein but referenced as if fully set out at this point.

The pipe of greatest interest herein is made of steel, thus it is customary to apply some sort of coating to the interior surface of each section of pipe to help protect it against corrosion by the fluids that flow through it. Typically this coating is applied to the interior of the pipe at the factory before the pipe leaves for installation. Imperfections in the coating can, of course, lead to subsequent corrosion and, ultimately, failure in the field. These imperfections might be due to problems at the factory, subsequent handling, installation, etc. Thus, it is common and desirable to determine the status of the coating as a final step after its installation.

The point of contact between adjacent pipe sections is also a potential source of failure in the field. In a typical arrangement, pipe sections are placed end to end and welded together to form a continuous pipeline. The welding at the joints (e.g., a "girth weld" or "field joint") is also subject to imperfections of different sorts that might have been created during the welding process. Further, the area near the end of each pipe section (e.g., "coating cutback") is typically not coated at the factory since such coating would be destroyed or corrupted by the welding process. Thus, there will be a gap in the coating of two pipe sections at their junction and it is desirable to coat at least that portion of the inside of each pipe after welding and before beginning to move fluids (to include gasses) through the pipeline. That operation must obviously be performed from inside the pipe and robotic solutions to perform this task are well known.

In the field multiple pipe sections are welded together to form a continuous pipeline that may extend for many miles. In some cases, the pipeline might be buried or submerged (e.g., placed on the ocean floor) where it may be difficult to access subsequently. Thus, it is imperative that the coating that is applied be unbroken or otherwise the useful life of the pipe section could be radically shortened. Of course, failure of a pipe section could result in release of its contents into the environment and/or could necessitate a costly repair or replacement of that section.

Imperfections in the coating of a steel pipe are typically sensed by way of a high voltage conductivity measurement. In a conventional arrangement, a robot is sent through the pipe section trailing behind it a wire that is placed in electronic communication with an uncoated section of the pipe. The robot then applies an electric voltage to a conductor (e.g., a brush with copper or brass strands) that is in contact with the inner surface of the pipe. Since the coating is generally non-conductive, pinholes, discontinuities, and other imperfections (i.e., "holidays") will allow a circuit to be completed which results in a lowered resistivity, thus making such imperfections sensible via conductivity measurements. Additionally, such an imperfection will typically also manifest itself as a spark between conductive brush and the pipeline wall, thereby providing a further indication of a holiday. Holidays may be marked after they are detected (e.g., by applying a small amount of highly visible paint or dye proximate to the pipe in the vicinity of the holiday) after which insertion of a second robot unit may be necessary in order to apply an additional coating to correct the problem area(s).

As is indicated above, it is conventional for such robots to drag behind them a long grounding wire which is attached to (or in electronic communication therewith) the bare steel of the pipe. This connection might be made by attaching the end of the wire opposite the robot to the bare steel of the pipe which is usually found on its exterior or on the inside of the pipe proximate to the point where the robot enters the pipeline (e.g., the outermost coating cutback end). Of course, this wire is subject to tangling or breaking and, if such happens, prior art robots must be withdrawn from the pipeline and the grounding wire repaired. Such removal and repair can take a considerable amount of time and, as might be suspected, a delay in completion of this stage of the pipeline construction will result in money lost to the operator.

Finally, a conventional approach to searching for holidays proximate a girth weld involves the use of a robot that has a conducting brush affixed to a rotating arm. As might be expected, in practice a charge is applied to the brush as it is swept through a 360° (more or less) arc. However, such an arrangement is not suitable for testing the entirety of the interior of the pipe. Further, a rotating arm is subject to a number of potential mechanical problems and, if such occurs, the robot will need to be withdrawn from the pipe and repaired. Such delays, of course, only increase the cost of the pipeline for the operator.

Thus, what is needed is an apparatus for locating holidays in coated pipe proximate a girth weld that does not suffer from the disadvantages of the prior art. It would be preferred that such a system would not utilize a grounding wire. Additionally, a new method of detecting holidays throughout the length of the pipe is needed that does not employ a rotating arm.

Heretofore, as is well known in the pipeline coating inspection arts, there has been a need for an invention that was not subject to the problems evident in the prior art. Accordingly, it should now be recognized, as was recognized by the present inventors, that there exists, and has existed for some time, a very real need for a system that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of the invention within the ambit of the appended claims.

SUMMARY OF THE INVENTION

There is provided herein a robot-based electrical system for locating holidays within coated pipe that does not utilize a grounding wire. In a preferred arrangement, the robot will carry a metal brush/capacitive pad combination. Preferably, the brush and pad will be extended to contact the interior coated surface of the pipe, and the brush will sweep the coated girth weld. After a high voltage (preferably DC) is applied to the brush/pad pair, a capacitor will be formed with the internal coating acting as the dielectric. If a holiday is not present, there will be no (or little) current observed. When the brush encounters a holiday, the capacitance formed will be momentarily shorted, and a high voltage will be rapidly presented on the pipe. The resulting current will preferably be detected via a microprocessor or other programmable logic device using circuitry connected to the capacitive pad. Additionally, in some preferred embodiments a video camera will be positioned on the robot so as to make it possible for a remotely situated operator to observe a corresponding spark if such is created. Preferably, the operator will have access to wirelessly transmitted real-time video of the robot's operations as well as some sort of real-time indication of the status of the brush.

According to another preferred variation, there is provided a wireless grounding system for locating holidays within coated pipe substantially similar to that described above, but wherein the brush preferably takes the form of a circumferential (i.e., non-rotating) brass brush that is positioned transverse to the center axis of the robot and is designed to be placed into contact with the inner circumference of the pipeline simultaneously. During inspection, the brush will preferably be designed to maintain constant contact with the interior of the pipe while the instant invention is moved therethrough. In this manner the entirety of the internal coating of the pipeline may be rapidly inspected.

In still another preferred arrangement, there is provided an apparatus for detecting holidays within coated pipe which utilizes the circumferential (preferably) brass brush of the previously embodiment, but which further utilizes a conventional grounding wire.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein.

Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which.

DESCRIPTION OF THE PREFERRED EMBODIMENTS

Figure 1:
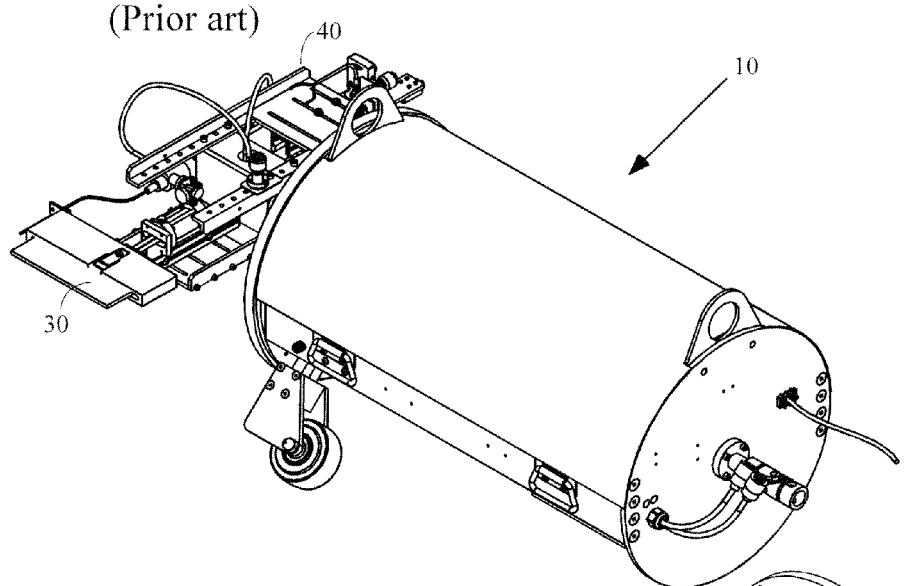
FIG. 1 depicts a prior art holiday location apparatus.

Referring now to the drawings, wherein the reference numerals indicate the same parts throughout the several views, there is provided an apparatus for locating flaws such as holidays in the coating of the interior of a pipe. According to a first preferred embodiment, there is provided an inspection robot that has an electrical system for locating holidays within coated pipe that does not utilize a grounding wire.

Turning first to FIG. 1, this figure illustrates a prior art robotic device 10 suitable for searching for holidays that occur in conjunction with pipeline internally coated girth welds. As is typical with such devices, it utilizes a brush 30 that is affixed to a rotatable arm 40. Additionally, a grounding wire is connected to the device 10 at point indicated on drawing and is terminated remotely against an uninsulated (e.g., uncoated) portion of the steel pipe. In operation, the device 10 is pulled or pushed into position. If the brush 30 is not already in contact with the interior of the pipe, the arm 40 will be extended until it is. An electrical voltage will be applied to the brush 30 and, at about the same time, the arm 40 will begin to rotate. Simultaneously, an internal electrical circuit will begin to monitor the voltage on the ground wire. This circuit typically utilizes a CPU/microprocessor of some sort which is preferably positioned onboard the device 10, although it could certainly be situated elsewhere in the train or any other location in electrical communication with the train's circuitry. Additionally, in some instances an optional video camera will transmit video of the rotating brush to an operator who is situated remotely from the device. If the brush encounters a holiday during its sweep, a drop in the impedance of the electrical circuit will be detected and the presence of a holiday will be communicated to the operator. Additionally, the holiday may be confirmable via the video link where encountering a holiday results in a visible spark between the brush 30 and the wall of the pipe.

Figure 2:
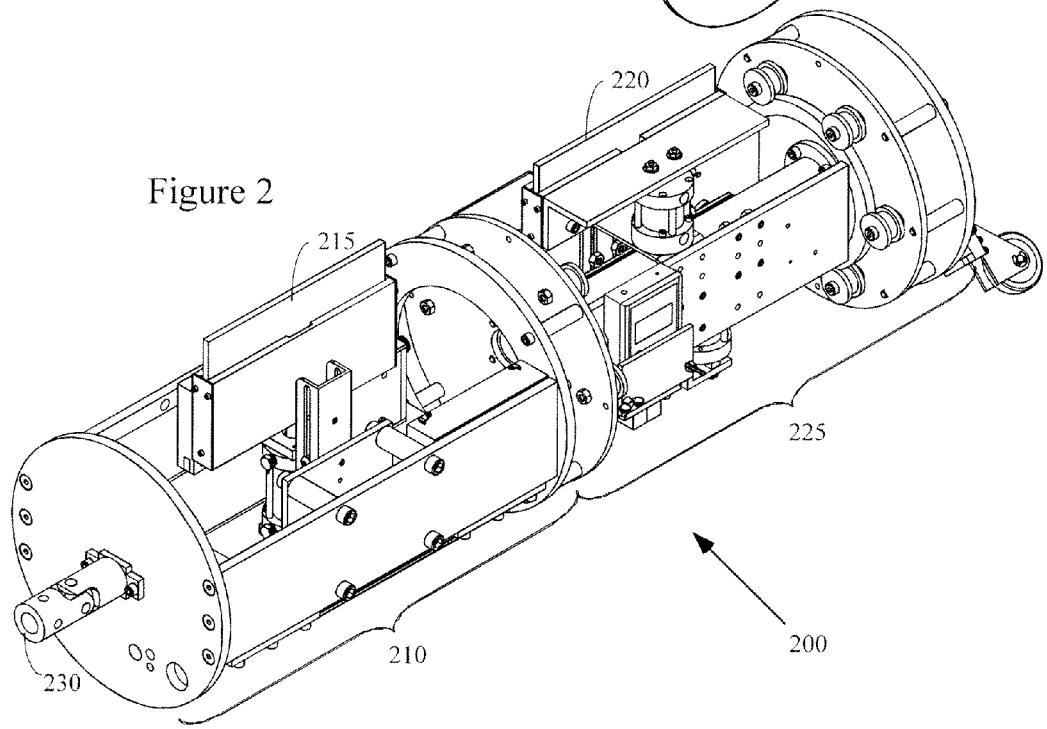
FIG. 2 illustrates a preferred embodiment of the instant wireless grounding holiday location device.
Figure 3:
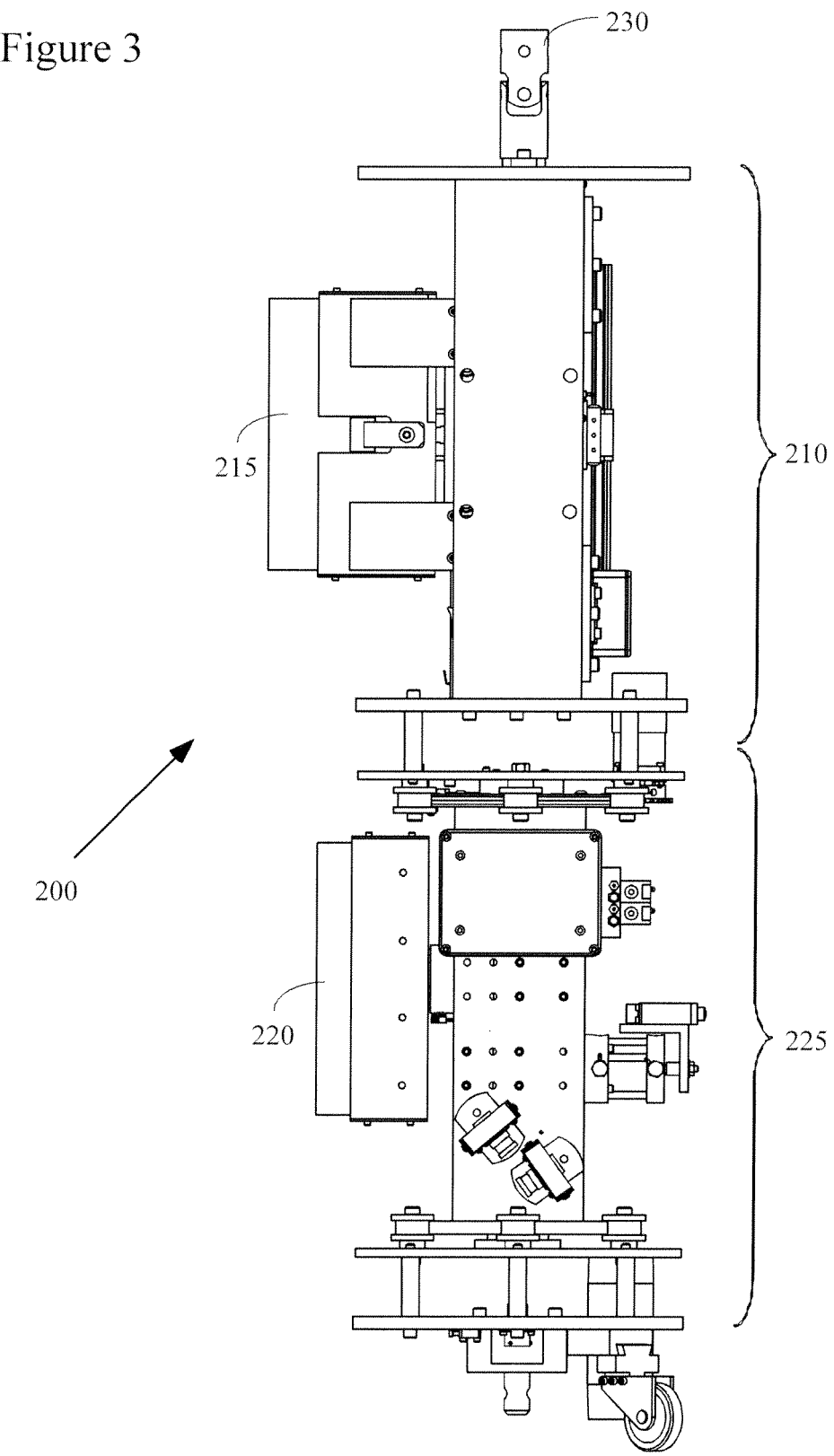
FIG. 3 illustrates a side elevational view of the embodiment of FIG. 2.

Turning now to FIGS. 2 and 3 which contain illustrations of a first preferred embodiment of the instant invention, in a preferred arrangement the instant invention will take the general form of a robot 200 that is moved within a pipe. The instant apparatus 200 could be configured to move under its own power within the interior of the pipe (e.g., an electrical motor to drive it through the pipe might be situated onboard) but in the preferred arrangement it will be towed or pushed by a separate engine or crawler (not shown). Preferably, the robot 200 and the engine that moves it will both be electrically powered.

The instant invention 200 will preferably be made to be part of a robot train that travels under its own power through a pipe, the train preferably containing the robot 200 as well as a portable power source, an engine for moving the train through the pipeline, various support electronics (e.g., video cameras, communications lines, etc.), and so on. Ultimate control of the robot 200 and the train will preferably be provided by a remotely situated operator who is in wired or wireless contact therewith. Connector 230 is provided to hitch the robot 200 to the next/adjacent device of in the robot train. Additionally, it is conventional to provide one or more on-board (or otherwise situated) microprocessors or other programmable logic devices that are designed to handle various general operations according to methods well known to those of ordinary skill in the art. In a preferred arrangement, one portion of the instant invention will be made rotatable (e.g., front member 225 in FIG. 2). That being said, those of ordinary skill in the art will recognize a rotating arm (e.g., as is shown in FIG. 1) might be utilized instead.

Incorporated into the rotating member 225 will preferably be a conductive brush 220 which is made of, for example, strands of brass wire or other conductive material (e.g., copper, aluminum, etc.). The instant brush 220 is designed to sweep across the interior surface of the pipe as it is rotated about the center axis of the apparatus 200. Of course, those of ordinary skill in the art will recognize that, although the element 220 is described as a conductive brush, that is only a preferred embodiment and other sorts of conductors might be used instead (e.g., a conductive pad, shoe, etc.). In practice, a pneumatic cylinder (not shown) will preferably be used to move the brush 220 into contact with the interior surface of the pipe and to withdraw it from such contact when the device needs to be relocated.

The preferred capacitive contact component, i.e., the capacitive coupling pad 215 of the instant invention, is carried in a separate nonrotating portion 210 of the device 200. As can be seen, the coupling member/capacitive pad 215 is preferably a stationary copper brush or, in some cases, a conductive shoe, etc., that is positioned to be in contact with the inner surface of the pipe. That being said, the exact form that the capacitive pad 215 takes is not important to the operation of the instant invention (e.g., it could be another brush). It is only necessary that it be in electrical communication with the interior of the pipe and at least somewhat electrically conductive.

In a preferred mode of operation, the instant invention 200 will be moved to the proximity of a girth weld or other section of the pipe that is to be tested. The arm on which the brush 220 is mounted will preferably be extended until it contacts the inner-coated surface of the pipe and the pad 215 will similarly be moved into contact with the wall of the pipe. Preferably a high voltage DC charge will be applied between the metal brush 220 and the pad 215, with the brush 220 having the higher potential. Then, the brush 220 will be rotated through at least 360° (e.g., the brush 220 may make multiple passes over the same surface) while it is monitored for changes in its electrical properties (described in greater detail below) that signal that a discontinuity or other imperfection in the coating has been encountered. Obviously, by utilizing the (assumed known) position of the device 200 within the pipe (e.g., its distance from the opening where it was inserted) together with the angle of the arm at the time the holiday was encountered it is possible to identify at least approximately the location that needs to be patched or otherwise repaired.

During the holiday sensing process, capacitances are formed between 220 and the pipe, and between 215 and the pipe, with the internal coating acting as the dielectric. The magnitude of the capacitances varies according to the contact area, and coating thickness and dielectric properties. According to standard electrical theory, the current through a capacitor is proportional to the rate change of voltage across it. During typical conditions without holidays, there is no current since the preferred voltage source is DC. When the brush 220 does encounter a holiday, the capacitance formed by 220 is momentarily shorted, and the high voltage is rapidly presented across the other capacitance formed by 215. The resulting current is detected with circuitry connected to the capacitive pad 215.

Figure 5:
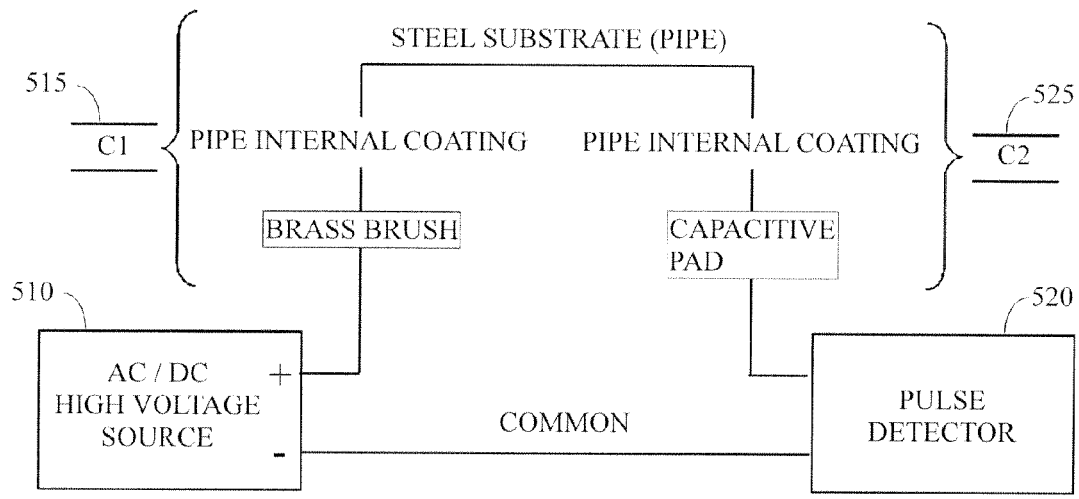
FIG. 5 contains a schematic circuit diagram that illustrates a preferred embodiment of the instant wireless grounding invention.

FIG. 5 contains a schematic illustration of the main electrical components of the instant invention. First, a DC high voltage source 510 is placed into electrical communication with the brush 220 which is, in turn, placed into contact with the coating on the interior of the pipe (a dielectric), the brush, internal pipe coating and steel substrate together forming a first capacitor C1 515. Note that the power source 510 might be situated within the robot 200 although it could also be located elsewhere in the train. The capacitive pad 215 is placed in contact with the pipe internal coating, thereby forming a second capacitor C2 525. Finally, a pulse detector 520 will be placed into electrical communication with the voltage source 510 and with the capacitive pad, with the pulse detector 520 preferably being locating within the robot 200 although it could readily be situated elsewhere according to techniques well known to those of ordinary skill in the art. All that is required is that the pulse detector be in direct or indirect electrical communication with the power source 510 and the capacitive pad 525.

In operation, the voltage source 510 will preferably generate a high voltage pulse of known amplitude. In the preferred arrangement, the pulse detector 520 will compare the amplitude of the received pulse which has passed through the two capacitors C1 and C2 with the known amplitude of the voltage source 510. Obviously, the presence of a holiday will tend to increase the amplitude of the received pulse by, e.g., removing or reducing the effect of the C1 (brush and coating) capacitor. A deviation in the observed amplitude of the pulse either as compared with a theoretical value or as compared with other/adjacent readings where the coating is intact will be used to identify holidays. Of course, those of ordinary skill in the art will recognize that a comparison between the amplitude of the transmitted and received pulse is just one way of examining the electrical signal for evidence of a holiday. More specifically, changes in other pulse characteristics such as frequency or phase shift, bandwidth change, etc., could alternatively be utilized to detect imperfections.

Preferably, the pulse detector 520 will utilize at least one microprocessor that is programmed to compare the transmitted and received pulses, detect signals consistent with the presence of a holiday and initiate action accordingly. For example, upon detection of a holiday the microprocessor might transmit a signal to the remote operator, initiate a process for marking the location of the holiday, etc.

Turning next to another preferred embodiment of the instant invention, there is provided a line travel inspection robot 400 that utilizes the wireless grounding system described above in combination with a four quadrant circumferential inspection brush, where "four quadrant" is used to indicate that one or more brush segments 410 are combined to cover all areas of the interior of a pipe. As a consequence, the instant embodiment 400 is well suited to continuously test the entire length of a pipe.

Figure 4:
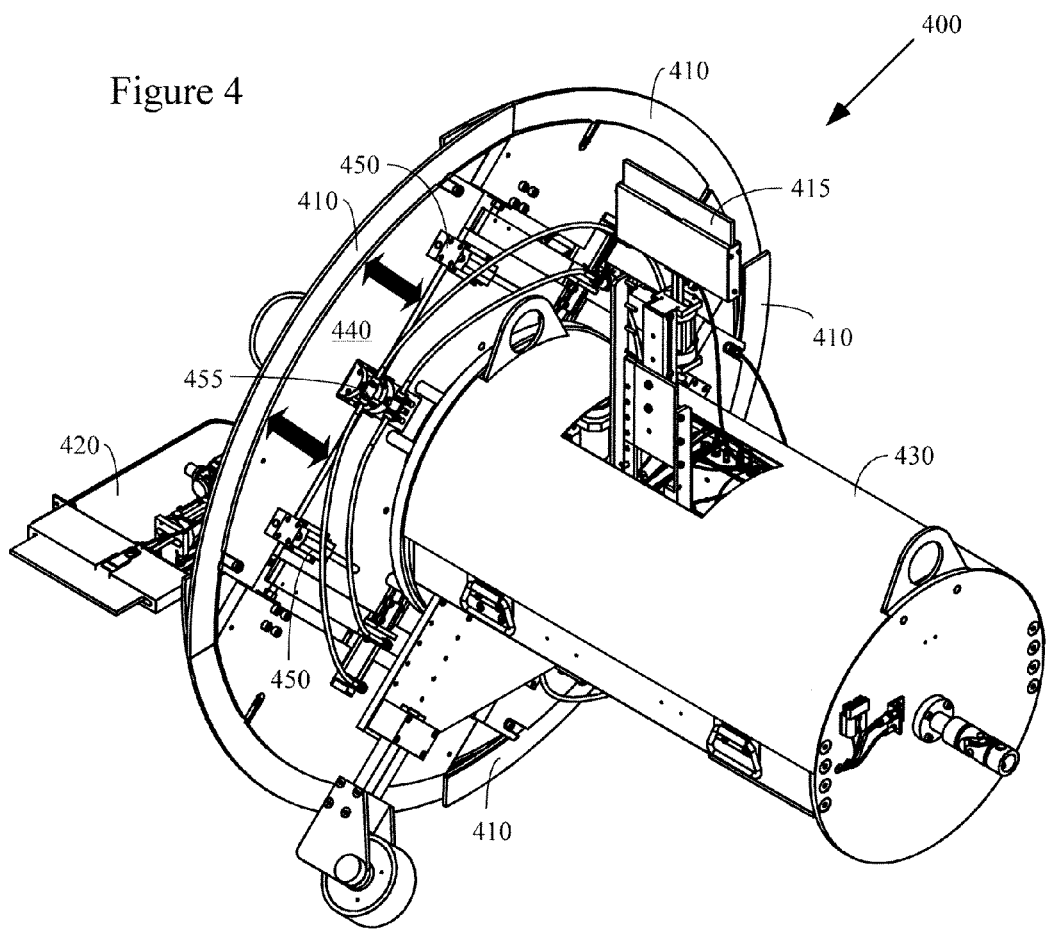
FIG. 4 contains an illustration of a preferred variation of a robotic line travel internal pipe coating inspection device.

FIG. 4 contains a preferred embodiment of this variation 400. Preferably, the robot 400 will utilize a circumferential brass brush 410 of the sort generally indicated in FIG. 4. As is indicated, the brush 410 will be mounted transversely to the robot center axis so that it can sweep substantially the entire inner surface of the pipe as the robot 400 moves through the pipe. Note that in the preferred arrangement the brush will be segmented into four pieces 410, thereby making it at least somewhat adjustable to match the diameter of the pipe that is under investigation by adjusting the amount of overlap between adjacent segments. That is, in the preferred arrangement the brush segments 410 will be movable toward and away from the longitudinal center of the device 400 thereby changing the radius of their contact area with the pipe. In the example of FIG. 4, each brush segment 440 can be adjusted in and out (i.e., away from and toward the pipe wall) by retraction/extension of this segment 440 via pneumatic (or electrical, etc.) extension elements 450/455. Preferably, the extension elements 450/455 will be extended and retracted via a slidable plunger or a similar mechanism. Once the brush segments 410 are in position against the inside wall of the pipe, the train will begin to move and the search for holidays will commence. In connection with this embodiment, it should be noted that when the term "transverse" is used herein to describe the orientation of the brush(s) 410 of the instant device 400, that term should be broadly construed to mean that the brush or brush segments 410 generally extend away from the center line of the robot 400 or pipe and toward its inner surface. Thus, this term should not be construed to require that the brush(s) 410 be oriented to be strictly perpendicular to the centerline.

Of course, the number of pieces 410 into which the brush is segmented is not critical to the operation of the instant invention and the number of segments might vary from as few as "one" (i.e., not segmented) to an arbitrarily large number. It is important, though, that the segments taken together substantially cover a full inner circumference of the interior of the pipe.

The instant invention will preferably utilize a capacitive pad 415 which will project through the housing 430 and will operate generally according to the scheme discussed previously. Additionally, in some preferred embodiments the invention 400 will be further equipped with a rotating arm/brush combination 420 that would, for example, allow it to examine girth welds as has been described previously in connection with embodiment 200. As such it is possible for the instant invention to perform both girth weld and full-length internal inspections with a single entry into the pipe.

In operation, the instant invention would be towed through the pipe by a crawler that contains an electric motor, with the instant embodiment 200 preferably being physically attached to the next element of the train via coupling 230. Upon receipt of a signal from the operator, the instant invention will apply a potential difference across the circumferential brush 410 and the capacitive pad 415 (e.g., perhaps on the order of about 2,000 volts as dictated by the coating manufacturer) and both will be placed in contact with the interior of the pipeline. As the device 400 is moved forward, in the preferred embodiment cameras and electronic circuitry will be used to monitor for the presence of holidays which will manifest as a spark or change in the electrical status of the brushes 410 and pad 415. Upon noting such, the instant invention will preferably mark that location (e.g., with a stripe of paint or some other agent) so that subsequently the imperfection can be patched according to methods well known to those of ordinary skill in the art.

Note that this embodiment is designed to continuously test longitudinal portions of the pipe for holidays, as compared with the previous embodiment (and, more generally, with the prior art) which must advance, stop, and rotate the section 220.

Figure 6:
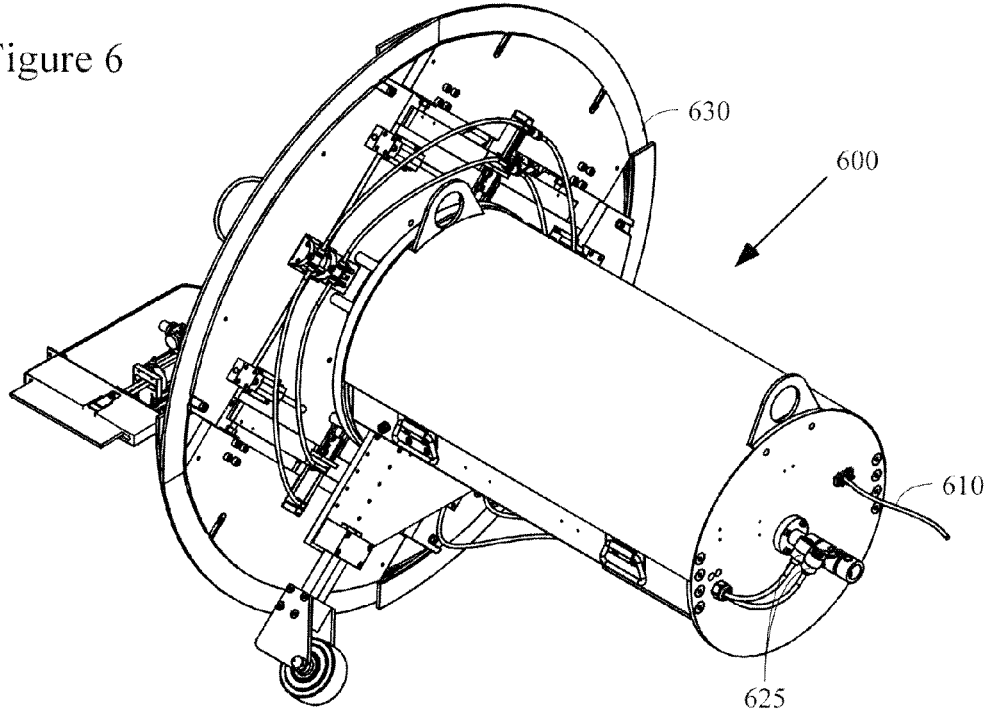
FIG. 6 contains an illustration of the embodiment of FIG. 4 in a wire-grounded version.

Turning to still another preferred embodiment, although the preferred embodiment of the instant invention 400 utilizes the wireless grounding approach discussed supra, an alternative is provided for finding holidays in a factory or otherwise coated pipe substantially as described above but wherein a grounding wire is utilized. In more particular and as is generally illustrated in FIG. 6, according to another preferred embodiment, there is provided an inspection robot 600 which is equipped with a circumferential brush 630 and a grounding wire 610. As has been explained previously, the grounding wire 610 typically travels from the robot 600 back to the entrance point of the pipeline where it is terminated against the pipe or against some other grounded conductive structure. Connectors 625 are part of the robot train circuitry which communicates information through the various devices of the robot train. In the preferred arrangement, these circuits are designed to provide access to power, handle signal transmission to and from the robot, and receive and send control information. This embodiment functions in a manner similar to that of a conventional holiday testing robot which utilizes a rotating brush in that a voltage is applied to the brush and it is monitored electronically (and visually via video in some cases) for sparks that would be indicative of breaks/imperfections (or holidays) in the internal pipe coating. The difference, of course, is that the instant embodiment is suitable for continuously testing large sections of pipe whereas a conventional robotic device must move to position, rotate the brush, test the coating, stop the brush rotation, move to the next location, etc. Obviously, the conventional approach is too time consuming to be of much use in larger sections of pipe.

As has been described previously, it is preferred that one or more on-board or otherwise situated microprocessors or other programmable devices be used to control the movement and other operations of the robot, detect holidays, communicate with the remote operator, transmit information to the operator (via video or other means), etc. When a holiday is discovered, it is preferable that the interior of the pipe be marked as has been described previously so that it can be subsequently located again for patching.

CONCLUSIONS

It should be noted that when the term "microprocessor" is used herein, that term should be broadly construed to include any sort of programmable or active device including, without limitation, microcontrollers, conventional microprocessors, gate arrays, programmable logic devices, etc. Additionally, even though the term microprocessor has been used in the singular here, that term should also be construed to cover instances where multiple microprocessors or other logical devices act in cooperation.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. An inspection robot for inspecting an interior coating of a pipeline for the presence of imperfections proximate to a weld seam of said pipeline, comprising:
   (a) a conductive brush positionable to be placed into contact with said interior coating of the pipeline, said brush being rotatable through an arc of substantially 360°;
   (b) a capacitive pad being positionable to be in contact with said interior coating of the pipeline;
   (c) a power source in electrical communication with said conductive brush and said capacitive pad, said power source being adapted for creating a pulsed current between said conductive brush and said capacitive pad; and,
   (d) a pulse detector in electronic communication with said power source and said capacitive pad, said pulse detector being adapted for detecting said pulsed current from said power source through said conductive brush and said capacitive pad.

2. The inspection robot according to claim 1, wherein said conductive brush is selected from a group consisting of a brass brush and a copper brush.

3. The inspection robot according to claim 1, wherein said pulse detector comprises a microprocessor in electronic communication with said capacitive pad and with said conductive brush.

4. The inspection robot according to claim 1, wherein said capacitive pad is selected from a group consisting of a conductive copper brush and a conductive shoe.

5. The inspection robot according to claim 1, wherein said capacitive pad is stationary.

6. A line travel inspection robot for inspecting an interior coating of a pipeline for the presence of imperfections, comprising:
(a) a circumferential conductive brush positionable to be placed into contact with the interior coating of the pipeline, said conductive brush being oriented transversely to a longitudinal center axis of said pipeline and extending through an arc of substantially 360°, thereby simultaneously contacting substantially all of an inner circumference of the pipeline;
(b) a capacitive pad, said pad being positionable to be in contact with the interior coating of the pipeline;
(c) a high voltage power source in electrical communication with said conductive brush, said power source being adapted for creating a pulsed current between said conductive brush and said capacitive pad; and,
(d) a pulse detector in electronic communication with said power source and said capacitive pad, said pulse detector being adapted for detecting a pulsed current from said power source through said conductive brush and said capacitive pad.

7. The line travel inspection robot according to claim 6, wherein said circumferential conductive brush is selected from a group consisting of a brass brush and a copper brush.

8. The line travel inspection robot according to claim 6, wherein said pulse detector comprises a microprocessor in electronic communication with said capacitive pad and with said conductive brush.

9. The line travel inspection robot according to claim 6, wherein said circumferential brush is segmented into at least four segments, each of said segments being movable away from and toward said pipeline centerline in order to place said each of said moved segments into contact with said inner circumference of the pipeline.

10. The line travel inspection robot according to claim 6, wherein said capacitive pad is selected from a group consisting of a conductive copper brush and a conductive shoe.

11. An inspection robot for inspecting an interior coating of a pipeline for the presence of imperfections, comprising:
(a) a robot body;
(b) a conductive brush supported by said robot body and positionable to be placed into contact with the interior coating of the pipeline, said brush being operable to examine an inner circumference of said pipeline;
(c) a capacitive pad, supported by said robot body, said pad being positionable to be placed in contact with the interior coating of the pipeline;
(d) a high voltage power source in electrical communication with said conductive brush and said capacitive pad, said power source being adapted for creating a pulsed current between said conductive brush and said capacitive pad; and,
(e) a pulse detector in electronic communication with said power source and said capacitive pad, said pulse detector being adapted for determining an amplitude of a pulsed current from said power source through said conductive brush and said capacitive pad.

12. The inspection robot of claim 11, wherein said conductive brush is rotatable through an arc of substantially 360°.

13. The inspection robot of claim 11, wherein said conductive brush is a circumferential conductive brush positionable to be placed into contact with the interior coating of the pipeline, said conductive brush being oriented transversely to a longitudinal center axis of said pipeline and conformable to extend through an arc of substantially 360°, thereby simultaneously contacting substantially all of an inner circumference of the pipeline.

14. An inspection robot according to claim 11, wherein said conductive brush is selected from a group consisting of a brass brush and a copper brush.

15. An inspection robot according to claim 11, wherein said pulse detector comprises a microprocessor in electronic communication with said capacitive pad and with said conductive brush.

16. The inspection robot according to claim 11, wherein said capacitive pad is selected from a group consisting of a conductive copper brush and a conductive shoe.

17. A line travel inspection robot for inspecting an interior coating of a metal pipeline for the presence of imperfections, comprising:
(a) a robot body;
(b) a circumferential conductive brush supported by said robot body and positionable to be placed into contact with the interior coating of the pipeline, said conductive brush being oriented transversely to a longitudinal center axis of said pipeline when so positioned and extending through an arc of substantially 360°, thereby simultaneously contacting substantially all of an inner circumference of the pipeline;
(c) a grounding wire positionable to be in electrical communication with an uncoated portion of the pipeline;
(d) a high voltage power source in electrical communication with said conductive brush and with said grounding wire; and,
(e) a conductivity detector in electronic communication with said power source, said grounding wire and said conductive brush, said conductivity detector being adapted for detecting a current from said power source through said grounding wire and said conductive brush.

18. The line travel inspection robot according to claim 17, wherein said conductive brush is comprised of a plurality of metal strands.

19. The line travel inspection robot according to claim 18, wherein said metal strands are selected from a group consisting of copper strands, brass strands, and aluminum strands.

20. The line travel inspection robot according to claim 17, wherein said circumferential brush is segmented into at least four segments, each of said segments being movable away from and toward said pipeline centerline in order to place said segment into contact with said inner circumference of the pipeline.

* * * * *